United States Patent [19]

Goins et al.

[11] Patent Number: 5,105,001
[45] Date of Patent: Apr. 14, 1992

[54] PHOSPHAZENE ANTIOXIDANTS

[75] Inventors: Dixie E. Goins; Hsueh M. Li, both of Baton Rouge, La.

[73] Assignee: Ethyl Corporation, Richmond, Va.

[21] Appl. No.: 584,315

[22] Filed: Sep. 18, 1990

[51] Int. Cl.$^5$ ............................................. C07F 9/6593
[52] U.S. Cl. ........................................ 558/80; 564/13
[58] Field of Search ............................. 558/80; 564/13

[56] References Cited

U.S. PATENT DOCUMENTS 3,446,876  5/1969  Breslow ................................. 558/80

OTHER PUBLICATIONS

*Plastics Engineering* 21(3), 20 (1975).
Scott, G. *Atmospheric Oxidation and Antioxidants;* Elsevier: New York, 1965.

*Primary Examiner*—Robert W. Ramsuer
*Assistant Examiner*—Michael G. Ambrose
*Attorney, Agent, or Firm*—Richard J. Hammond

[57] ABSTRACT

Novel substituted phosphazene compounds are disclosed having the formula

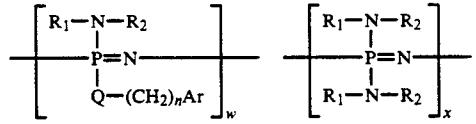
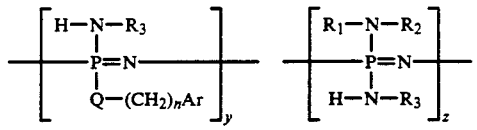

wherein w, x, y and z are integers the sum of which is from 3 to 6 with the proviso that w is at least 1 but equal to or less than $(w+x+y+z)-1$, x is from 1 to 5, y and z are from 0 to 2;

$R_1$ and $R_2$ are the same or different and are $C_1$ to $C_6$ linear or branched alkyl;

$R_3$ is an unsubstituted or substituted aryl and n is 0 or an integer from 2 to 6; Q is —O—,

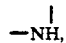

—NH,

—NR— or —S—; Ar is

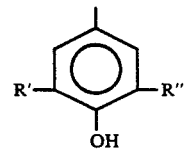

R' and R" are the same or different and are $C_1$ to $C_6$ linear or branched alkyl, with the proviso that R" can also be hydrogen, wherein $R_1$ and $R_2$ are the same or different $C_1$ to $C_4$ linear or branched alkyl group and n is 0 or an integer from 2 to 6. These compounds display good solubilities in both organic and aqueous systems. Accordingly, they act as antioxidants in adhesive, sealant and coating compositions.

5 Claims, No Drawings

PHOSPHAZENE ANTIOXIDANTS

The present invention relates to a novel class of compounds and to their use as antioxidants. More particularly, this invention is concerned with a class of amino and hindered phenolic substituted phosphazenes and the employment of these compounds as antioxidants for organic materials. These compounds provide the basis for water soluble antioxidants in aqueous-based compositions.

During the refining, manufacturing and blending processes, and during subsequent storage and handling operations, it is unavoidable that hydrocarbon fuels or their ingredients, such as cracked blending stocks, or the highly olefinic stocks for reforming and alkylation, are brought into contact with oxygen. The result of such contact is the formation, by oxidation or polymerization or a combination thereof, of gummy materials. The presence of such gummy materials in fuels for spark ignition engines causes valve sticking, lowers spark plug efficiency and produces piston varnish and associated troubles. Such deteriorated fuels, when used in diesel engines, interferes with the operation of the fuel filters and injectors.

Because of the specifications imposed on fuels by the rigid requirements of present day engines, particularly aircraft engines, it is essential that any material capable of protecting such fuels against deterioration be effective in extremely small quantities, on the order of one pound of additive per five thousand gallons of fuel, so that secondary problems do not arise through their use.

To a greater or lesser degree, all polymers are susceptible to degradation by oxygen or trace amounts of ozone. This degradation, which is caused by oxidation, can lead to discoloration, impairment of physical properties, and eventually to total mechanical failure. Although commercial polymers encompass a wide range of chemical compositions and structures, the basic mechanism of their oxidative degradation is similar to that for the simpler hydrocarbons. Therefore, many polymeric materials in extensive uses require protection from the adverse effects of contact with oxygen.

One such class of polymeric materials is the elastomers, both natural and synthetic. Upon absorption of oxygen such elastomers deteriorate prematurely. They lose tensile strength and flexibility and become discolored and embrittled. This absorption can occur during manufacturing operations, fabrication, storage or use. While certain materials have been used for the protection of these elastomers from the deleterious action of oxygen, many of such protective substances possess the serious disadvantage, particularly with respect to light colored stocks, that the decomposition products are themselves colored and hence interfere with the color fastness of the stocks being protected.

Further examples of materials which require protection from the effects of oxygen include certain foodstuffs, such as animal and vegetable oils and fats, which upon exposure to oxygen develop rancidity, color and odor. Still further examples include mineral oils, lubricating oils, soaps, and diverse synthetic unsaturated organic materials.

Among the commercially important compounds that inhibit the deleterious effects of oxygen on organic compounds are the hindered phenols and secondary alkyaryl and diaryl amines such exemplified by 2,6-di-t-butyl-4-methylphenol and N,N-di-p-t-butylphenylamine. See for example Plastics Engineering, 21 (3), 20, 1975 and G. Scott *Atmospheric Oxidation and Antioxidants.* Elsevier Publishing Company, Inc., New York, 1965. These, and similar compositions, are effective antioxidants in organic systems. However, their use in aqueous-based compositions is limited. And some of them do not have satisfactory high temperature aging resistance due to the ease with which they are removed from polymers containing them by volatilization or extraction during use.

U.S. Pat. No. 3,446,876 discloses polyphosphazene antioxidants, particularly hexakis(2,5-di-tert-alkyl-hydroxyphenoxy)cyclotriphosphazatrienes and octakis(3,5-di-tertalkyl-4-hydroxyphenoxy)cyclotetraphosphazatetraenes. While effective antioxidants, these compounds are relatively high melting compounds. Their incorporation into lower melting polymers and compositions is different and provides non-uniform effectiveness.

It is an object of this invention to provide means for protecting organic substances which deteriorate in or are affected adversely by oxygen.

It is a further object of this invention to provide a class of substances which are compatible with organic substances and will prevent the formation of gummy oxidation and polymerization products of unstable organic substances on contact with oxygen.

Another object of this invention is to provide means for stabilizing hydrocarbon fuels for internal combustion spark and compression ignition engines during the manufacturing, handling and storage of such fuels prior to their use.

A further object of this invention is to provide means for protecting foodstuffs and other perishable natural or synthetic organic materials from the adverse effects of contact with oxygen.

It is an additional object of this invention to provide means for preventing embrittlement, discoloration, loss of tensile strength and other harmful effects in elastomers during the milling, compounding, fabrication, storage, handling and use of such elastomer stocks.

It is another object of this invention to provide a means for preventing the oxidative degradation of aqueous-based organic compounds.

Still further objects of this invention will appear from the description of this invention as hereinafter disclosed.

The objectives of the present invention are accomplished by providing a novel composition of matter having the general

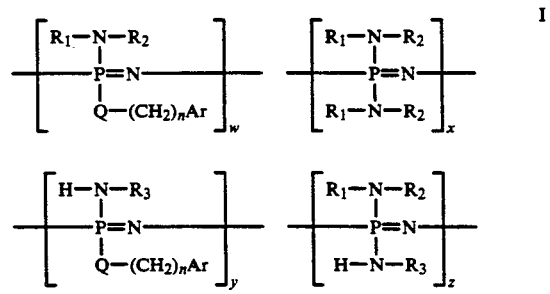

wherein w, x, y and z are integers the sum of which is from 3 to 6 with the proviso that w is at least 1 but equal to or less than $(w+x+y+z)-1$, x is from 1 to 5, y and z are from 0 to 2, $R_1$ and $R_2$ are the same or different and are $C_1$ to $C_6$ linear or branched alkyl, $R_3$ is an unsubstituted or substituted aryl, n is 0 or an integer from 2 to 6, Q is —O—, —NH—,

or —S—; and Ar is

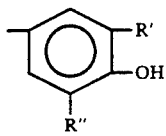

where R' and R" are the same or different and are hydrogen or $C_1$ to $C_6$ linear or branched alkyl, with the proviso that R' is never hydrogen.

Preferably $R_1$ and $R_2$ are the same or different and are $C_1$ to $C_6$ linear or branched alkyl, $R_3$ is $C_6$ to $C_9$ aryl unsubstituted or substituted with methyl, ethyl, n-propyl or i-propyl, (w+x+y+z) is equal to 3 and Ar and n are as previously defined.

A most preferred embodiment of the present invention are compositions where $R_1$, $R_2$, R' and R" are the same and are $C_1$ to $C_4$ linear or branched alkyl, $R_3$ is unsubstituted phenyl, n is 0 or 2 to 3, and the sum of w, x, y and z is from 3 to 4.

Of the most preferred compounds of the present invention, preferred are those compounds where $R_1$ and $R_2$ are $C_1$ or $C_2$ alkyl, $R_3$ is phenyl, R' and R" are tert-butyl, n is 0, w is 1 to 2, x is 1 to 2 and the sum of w, x, y, and z is 3.

Particularly preferred are cyclic compounds of the formula

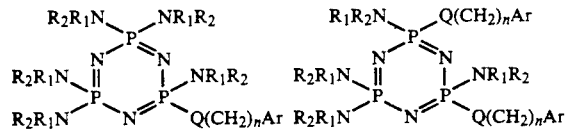

where $R_1$, $R_2$, Q, n and Ar are as previously defined.

In such cyclic compounds, it is preferred that $R_1$ and $R_2$ are $C_1$ to $C_4$ linear or branched alkyl. The most preferred compounds are those where $R_1$ and $R_2$ are methyl, n is 0, R' and R" are tert-butyl and Q is —O—.

The novel phosphazene antioxidants of the present invention are prepared by a two-step reaction sequence. The first step is the reaction of cyclophosphonitrilic halide [e.g. $(N=PCl_2)_3)$] with HQ—$(CH_2)_n$—Ar (Ar and Q are as previously defined) in the presence of a base such as triethylamine or with MQ—$(CH_2)_n$—Ar in an appropriate solvent to yield partially substituted cyclophosphazene. The first step of the reaction is illustrated by the following equation:

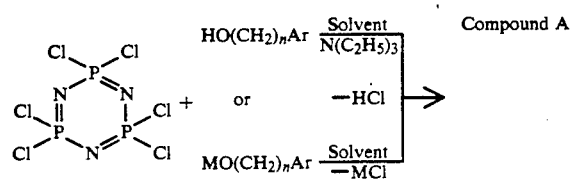

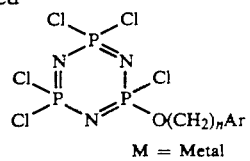

M = Metal

The second step is the reaction of the partially substituted phosphazene (Compound A) with an excess amount of same or different diamines or a mixture of mono- and diamines in the same solvent to yield a fully substituted phosphazene (Compound B). The second step of the reaction is illustrated by the following equation:

Compound A + $HN(CH_3)_2$ $\xrightarrow[-(CH_3)_2NH \cdot HCl]{\text{Solvent}}$ Compound B
(excess)

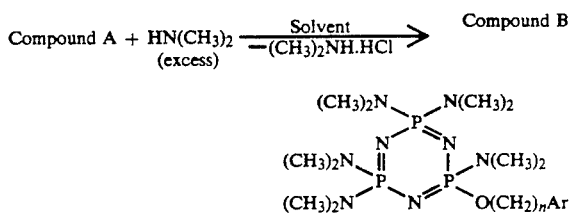

Metal derivatives of the aryloxides or alkoxides may be prepared by reacting the metal or metal hydride with the phenols or alcohols in any convenient manner. Of the metals, the alkali metals are preferred. Sodium and potassium are highly preferred because of their availability. Sodium is more preferred because of its reactivity and relative inexpensiveness. Typical solvents which can be employed are p-dioxane and tetrahydrofuran (THF).

In many instances, the reaction is quite rapid, being exothermic at the beginning, and requires no heating. After mixture of the reactants is complete, it may be convenient to heat the resultant reaction mass and hold it at reflux temperature for such time as analysis indicates complete reaction. Reaction times in the range of from about 6 to about 15 hours can be used. This is somewhat dependent upon the reaction temperature which is usually within the range of ambient to 110° C.; more preferably from about 50° C. to 110° C.

The phosphonitrilic halide starting material useful in this invention can be obtained from phosphonitrilic chlorides $(N=PCl_2)_n$ or phosphonitrilic bromides $(N=PBr_2)_n$ where n is about 3 to about 6. Because of their more ready availability, the phosphonitrilic chlorides are preferred. Phosphonitrilic chlorides used to prepare the phosphazene compounds of this invention can be produced by:

a) reacting $PCl_5$ with ammonium chloride; U.S. Pat No. 3,367,750;

b) reacting $PCl_5$ with ammonia, U.S. Pat No. 3,656,916;

c) reacting phosphorus trichloride, chlorine and ammonia; U.S. Pat No. 4,537,755.

The phosphonitrilic chlorides produced by the above reactions are a mixture having the formula $(N=PCl_2)_n$ wherein n is usually from 3 to about 6. The lowest value of n is 3, for the trimer, which is the most usual form. The trimer can be isolated from the mixture by fractional distillation or solvent extraction or both. The trimer is currently commercially available. Although the mixture, $(N=PCl_2)_n$, can be used to prepare the phosphazene antioxidant compounds, the trimer is preferred mainly because it is easier to tailor the composition of the substituted phosphazene compound from the trimer than from the mixture.

The mono- and diamines which may be employed in this invention may be aliphatic or aromatic or mixed alkylarylamine such as:
dimethylamine;
diethylamine;
dipropylamine;
N-ethylmethylamine;
N-methylaniline;
isopropylamine;
isobutylamine;
aniline;
p-toluidine;
p-anisidine (4-methoxyaniline);
and the like.

To incorporate a hindered phenolic group into the phosphazene structure, a compound which contains an active hydrogen which is more reactive than the hydrogen of the hindered phenol is needed. Such compounds have the following general structure

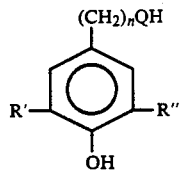 (I)

wherein R' and R" are as earlier defined and Q is —O—, $$-\overset{|}{N}H,$$

—NR— or —S—, and R is $C_1$ to $C_3$ linear alkyl. The hydrogen attached to Q is more reactive than the hydrogen of the sterically hindered —OH group so that —QH group, not the hindered —OH, will be involved in the reaction with the phosphonitrilic chloride molecule. Examples of such compounds (I) are:
2,6-di-tert-butyl-4-hydroxyphenol;
2-(3,5-di-tert-butyl-4-hydroxyphenyl) ethanol;
4-amino-2,6-di-tert-butylphenol;
4-amino-2,6-di-isopropylphenol; and the like The phosphazene antioxidants of this invention are designed to be relatively low in cost and are either low melting point solids or liquids at ambient temperature to provide easier or better mixing with the organic materials (petroleum products, lubricants, adhesives, plastics, rubber, etc.) which need protection against atmospheric oxidation. Relatively low cost dialkylamines are used as major substituents of the phosphazene antioxidants in this invention for the above mentioned purposes. Another advantage of using dialkylamine as a major substituent is that a water soluble phosphazene antioxidant/HCl adduct can be obtained.

The compounds of this invention and the methods for their preparation are illustrated by the following specific examples:

EXAMPLE 1

Reaction of (NPCl$_2$) with
2-(3,5-di-tertbutyl-4-hydroxyphenyl)ethanol and dimethylamine.

13.9 gm (4 mmol) of hexachlorocyclotriphosphazene was dissolved in dried THF and 2.0 gm (8 mmol) of 2-(3,5-di-tertbutyl-4-hydroxyphenyl)ethanol was dissolved in 25 mL of THF. These two solutions were added into a 250 mL, three-necked round bottom flask equipped with a magnetic stirrer, reflux condenser, thermometer and addition funnel. To the stirred reaction medium, 0.89 gm (8.8 mmol) of triethylamine was added dropwise from the addition funnel. The mixture was stirred at ambient temperature for about 12 hr. The precipitated salt was filtered and washed with dried THF. The filtrate was poured back to the reactor and an excess of dimethylamine was added gradually into the reactor from 0° to room temperature for one hour and then at 45°-60° C. for about one hour. The reactor was allowed to cool to ambient temperature. The precipitated salt was filtered and washed with THF. The filtrate was then distilled to remove the solvent and residual triethylamine and dimethylamine. About 0.18 g (7.5% yield) of wax-like product was obtained. The LC/MS and $^{31}P$ NMR analyses indicated that the product is $P_3N_3[N(CH_3)_2]_5[2-(3,5-di-tert-4-hydroxyphenyl)ethoxy]$.

EXAMPLE 2

Reaction of $P_3N_3Cl_6$ with
3,5-di-tert-butyl-4-hydroxyphenol and dimethylamine.

$P_3N_3Cl_6$ (9.75 g, 28mmol), sodium hydride (0.96 g, 40 mmol) and 60 g of dry 1,4-dioxane were placed in a 250 mL, three-neck, round bottom flask which was equipped with a condenser, thermometer, addition funnel, and magnetic stirrer. To the above stirred mixture, a solution of 3,5-di-tert-butyl-4-hydroxyphenol (6.66 g, 30 mmol) in 60 g of dioxane was added slowly over a period of one hour under nitrogen atmosphere at 24° C. to 30° C. Temperature was controlled by using an icebath. The bubbling of hydrogen gas indicated the formation of sodium salt of 3,5-di-tert-4-hydroxyphenol. The reaction mixture was then heated at 50° C. for an additional two hours. A little sample of the reaction solution was removed for $^{31}P$ NMR analysis to check the conversion.

About 50% of the hindered phenol was reacted. The reaction mixture was cooled to 10°-12° C. in an icebath. Additional 0.96 g of NaH was added very slowly into the stirred reaction medium in 30 minutes. the reaction mixture was stirred at 12° to 22° C. for 2 hours, 22° to 53° C. for 3 hours, and then cooled to 10°-12° C. An excess amount of dimethylamine was then added over a period of six hours and the temperature was gradually raised from 10° C. to about 90° C. The heating device was turned off and the reaction medium was allowed to cool to ambient temperature under stirring. The $^{31}P$ NMR analysis of the reaction medium showed that the reaction was essentially complete. Dioxane was stripped off and diethyl ether (150 mL) was added. The salt (NaCl) formed was removed by filtration and rinsed twice with 20 mL of diethyl ether. The combined etheral solution was evaporated under vacuum to give 13.8 g (83.1% yield) of a pink solid. The overall yield of this reaction was about 93% (83.1% plus about 10% due to sampling for analysis). The NMR and mass spectra analysis indicated that the product consisted of 85% mono-(3,5-di-tert-butyl-4-hydroxyphenoxy)-pentakis(-dimethylamino)cyclotriphosphazene.

A DSC analysis indicated that the above product melted at 81° C. and started to decompose at 351° C.

Thin layer chromatography was employed to purify the pink product. A nearly colorless solid was obtained.

The purified product was soluble in various organic solvents such as hexane, cyclohexane, dioxane, ethyl ether, methanol, THF, chloroform and a mixture of methanol and water, but was very slightly soluble in water.

EXAMPLE 3

Preparation of phosphazene antioxidant/HCl adduct.

Aqueous HCl solution (0.25 g, 37 wt %, 2.5 mmol HCl) was added at 23° C. to a solution of the product of Example 3 (1.45 g, 2.5 mmol) in diethyl ether (10 g) under stirring. Solid mass started to precipitate out of ether solution after 15 minutes. The reaction mixture was stirred at ambient temperature overnight. The ether layer was decanted and the solid adduct was rinsed with fresh diethyl ether (4 g). The ether layer was decanted and the solid mass was dried to yield 1.15 g of pale yellow powder product. The DSC analysis showed that the obtained mono-(3,5-di-tert-butyl-4-hydroxyphenoxy)tetrakis(dimethylamino) cyclotriphosphazene/HCl adduct melted at 206.6° C. The adduct is soluble in water to yield about 3 wt % aqueous solution.

EXAMPLE 4

Evaluation of phosphazene antioxidant.

The cyclotriphosphazene antioxidant prepared in Example 3 was evaluated as a stabilizer in a New Technology polypropylene (Profax 6501) at 260° C.-30 RPM single screw extrusion. The melt flow index (MFI) and Yellowness Index of the antioxidant in Profax 6501 were measured. Vitamin E, which is very effective antioxidant, was used as a reference tor comparison. The results are shown in Table I.

TABLE I

Evaluation of mono-(3,5-di-tert-butyl-4-hydroxyphenoxy)-tetrakis(dimethylamino)cyclotriphosphazene as a stabilizer in polypropylene Profax 650.
Formula: Profax - 600 g
Antioxidant - 0.1%
Calcium stearate - 0.05%
SS - Extrusion (Brabender) at 260° C. - 30 RPM

| Antioxidant | MFI at 230° C.-2160 g Load Extrusion Passes | | | Yellowness Index Extrusion Passes | |
|---|---|---|---|---|---|
| | 1st Pass | 3rd Pass | 5th Pass | 1st Pass | 5th Pass |
| Vitamin E | 5.2 | 8.7 | 11.6 | 11.3 | 15.9 |
| Product of Example 3 | 5.2 | 7.6 | 11.2 | 6.8 | 11.2 |

The preliminary test results show that the product of Example 3 is slightly better than Vitamin E in controlling melt flow polypropylene and significantly better than Vitamin E in controlling yellowness index.

We claim:

1. An organic solvent-soluble phosphazene antioxidant compound of the formula

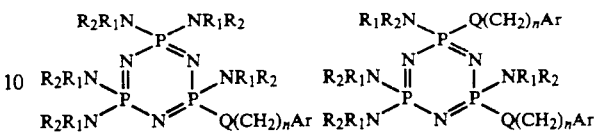

wherein $R_1$ and $R_2$ are the same or different and are $C_1$ to $C_6$ linear or branched alkyl, Ar is

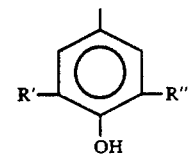

where R' and R" are the same of different and are hydrogen or $C_1$ to $C_6$ linear or branched alkyl, with the proviso that R' is never hydrogen, Q is —O—, —NH—,

or —S—, where R is a $C_1$ to $C_3$ alkyl group, where R is a $C_2$ to $C_3$ alkyl group, and n is 0 or an integer from 2 to 6.

2. The organic solvent soluble phosphazene antioxidant according to claim 1 wherein $R_1$ and $R_2$ are same or different and are $C_{1-C2}$ alkyl, $R_3$ is phenyl, R' and R" are t-butyl, n is 0, w is 1 to 2, x is 1 to 2, and the sum of x, y, z, and w is 3.

3. The phosphazene antioxidant according to claim 1 wherein $R_1$ and $R_2$ are methyl and Ar and n are as previously defined.

4. The phosphazene antioxidant according to claim 3 wherein Ar is p-hydroxy substitute $C_6$ aryl further substituted with tert-butyl groups ortho to the hydroxy group, n is 0 and Q is —O—.

5. A water soluble phosphazene antioxidant/HCl adduct where the phosphazene antioxidant is defined in claim 1.

* * * * *